United States Patent
Shroff et al.

(10) Patent No.: US 8,993,788 B2
(45) Date of Patent: Mar. 31, 2015

(54) CHIRAL INTERMEDIATES USEFUL FOR THE PREPARATION OF HYDROXYPHOSPHINE LIGANDS

(75) Inventors: Jaidev Rajnikant Shroff, Maharashtra (IN); Vikram Rajnikant Shroff, Maharashtra (IN); Birja Shanker, Maharashtra (IN)

(73) Assignee: UPL Limited, Mumbai, Maharashtra (IN)

( * ) Notice: Subject to any disclaimer, the term of this patent is extended or adjusted under 35 U.S.C. 154(b) by 0 days.

(21) Appl. No.: 13/882,580

(22) PCT Filed: Nov. 1, 2011

(86) PCT No.: PCT/IB2011/002587
§ 371 (c)(1),
(2), (4) Date: Apr. 30, 2013

(87) PCT Pub. No.: WO2012/059807
PCT Pub. Date: May 10, 2012

(65) Prior Publication Data
US 2013/0217900 A1    Aug. 22, 2013

(30) Foreign Application Priority Data

Nov. 2, 2010 (IN) .......................... 3045/MUM/2010
Nov. 2, 2010 (IN) .......................... 3046/MUM/2010

(51) Int. Cl.
| | | |
|---|---|---|
| *C07C 31/135* | (2006.01) | |
| *C07F 9/50* | (2006.01) | |
| *C07C 43/21* | (2006.01) | |
| *C07D 309/12* | (2006.01) | |
| *C07F 7/08* | (2006.01) | |
| *C07C 29/149* | (2006.01) | |
| *C07C 29/64* | (2006.01) | |
| *C07C 67/08* | (2006.01) | |
| *C07C 67/14* | (2006.01) | |
| *C07D 309/10* | (2006.01) | |
| *C07D 309/30* | (2006.01) | |

(52) U.S. Cl.
CPC ............. *C07C 31/135* (2013.01); *C07C 29/149* (2013.01); *C07C 29/64* (2013.01); *C07C 67/08* (2013.01); *C07C 67/14* (2013.01); *C07D 309/10* (2013.01); *C07D 309/12* (2013.01); *C07D 309/30* (2013.01); *C07F 9/5027* (2013.01); *C07C 43/21* (2013.01); *C07F 7/0818* (2013.01); *C07B 2200/07* (2013.01); *C07C 2101/10* (2013.01)
USPC ............. 549/416; 568/17; 568/661; 568/838; 556/488

(58) Field of Classification Search
CPC . C07B 2200/07; C07F 7/0818; C07F 9/5027; C07C 29/64; C07C 67/14; C07C 2101/10; C07C 29/149; C07D 309/10; C07D 309/12; C07D 309/30
USPC ............. 549/416; 568/17, 661, 838; 556/488
See application file for complete search history.

(56) References Cited

U.S. PATENT DOCUMENTS

2006/0089469 A1* 4/2006 Komarov et al. ............. 526/138

FOREIGN PATENT DOCUMENTS

| WO | WO 2008/092924 | 8/2008 |
| WO | WO 2009/136409 | 11/2009 |

OTHER PUBLICATIONS

Greene, T.W., "Greene's protective groups in organic synthesis. John Wiley & Sons", 2006, Chapter 2, p. 16-366.*
March, J., "March's advanced organic chemistry: reactions, mechanisms, and structure." John and Wiley Sons, Inc., New York, 2007, Chapter 10, p. 425-656.*
International Search Report and Written Opinion from International Application No. PCT/IB2011/002587 mailed Jan. 25, 2012.
Jarowicki et al, "Protecting Groups", *J. Chem. Soc., Perkin Trans. 1*, 1998, pp. 4005-4037.
Komarov et al., "A new hydroxydiphosphine as a ligand for Rh(I)-catalyzed enantioselective hydrogenation", *Tetrahedron: Asymmetry*, vol. 13, 2002, pp. 1615-1620.
Morrison et al., "Asymmetric Homogeneous Hydrofenation", *Advances in Catalysis*, vol. 25, 1976, pp. 81-124.

* cited by examiner

*Primary Examiner* — Noble Jarrell
*Assistant Examiner* — John Mauro
(74) *Attorney, Agent, or Firm* — Merchant & Gould P.C.

(57) ABSTRACT

A compound of formula (I), wherein $R^1$ is hydrogen or a hydroxyl protecting group; and $R^2$ and $R^3$ are same or different and are independently selected from halogen or —O—$SO_2$—X; wherein X is —$C_1$-$C_4$ alkyl; $C_1$-$C_4$ alkyl substituted with one or more halogen; or substituted or unsubstituted phenyl wherein said phenyl substituent is selected from halogen, nitro and $C_1$-$C_4$ alkyl; provided that when $R^3$ is bromine, X is not p-toluoyl; and a process for the preparation thereof.

9 Claims, No Drawings

CHIRAL INTERMEDIATES USEFUL FOR THE PREPARATION OF HYDROXYPHOSPHINE LIGANDS

This application is a National Stage Application of PCT/IB2011/002587, filed 1 Nov. 2011, which claims benefit of Serial No. 3045/MUM/2010, filed 2 Nov. 2010 in India and Serial No. 3046/MUM/2010, filed 2 Nov. 2010 in India and which applications are incorporated herein by reference. To the extent appropriate, a claim of priority is made to each of the above disclosed applications.

FIELD OF THE INVENTION

The invention relates to novel intermediates which are useful in the preparation of hydroxyphosphine ligands and a process for the preparation thereof. More particularly, the present invention relates to novel intermediates useful for the preparation of hydroxyphosphine ligands which are used as ligands on transition metals in metal catalyzed asymmetric synthesis, in particular hydrogenations and a process for the preparation thereof.

BACKGROUND AND PRIOR ART

There is a growing need for the synthesis of chiral compounds which are used as pharmaceuticals and agrochemicals. Classical methods of separation of the optical isomers are one aspect of the synthesis, which result in the cumbersome process of resolution and racemization, often making the process uneconomical. Another way of preparing the chiral compound is to use chiral synthesis approach which is being increasingly used as preferred industrial method. This synthesis involves the use of chiral reagents, and especially use of chiral catalysts to bring about the desired transformation.

Various catalytic systems have been used for different types of chiral transformations. Some of these systems use bidentate organophosphorous compounds which have attained great importance as ligands in homogeneous catalysis. Hydroxyphosphine compounds of Formula IA are useful as ligands on transition metals in metal catalyzed asymmetric reactions such as hydrogenation, hydroformylation, rearrangement, allylic alkylation, cyclopropanation, hydrosilylation, hydride transfers, hydroborations, hydrocyanations, hydroxycarboxylations, and so on (ref. US 2006/0089469 A1).

Formula IA

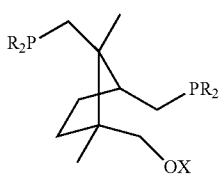

US 2006/0089469 discloses compound of Formula IA and the process of making the same.

WO 2009136409 discloses a process for the asymmetric hydrogenation of a prochiral ketimine to get a chiral amine wherein the said transformation is effectively carried out in the presence of iridium and rhodium complexes containing the ligand of Formula IA, which upon reaction with haloacetyl chloride affords various haloacetanilide herbicides. In particular, the preferred ligand is [(1R,2R,3S)-1,2-dimethyl-2,3-bis(diphenyl phosphine methyl) cyclopentyl]methanol (herein after referred to as compound of Formula A). However, this publication does not teach an industrially feasible route for the synthesis of said compound of formula A.

Formula A

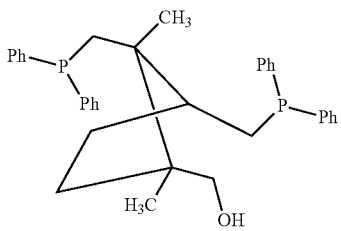

WO 2008092924 discloses a process for selectively synthesizing a stereoisomer of zilpaterol by reacting 4,5-dihydro-imidazo[4,5,1-jk][1]benazepine-2,6,7[1H]-trion-6-oxime with $H_2$ in the presence of a catalyst to selectively form a stereoisomer of 6-amino-7-hydroxy-4,5,6,7-tetrahydroimidazo[4,5,1-kj][1]-bencazepin-2[1H]-one, which, in turn is converted to zilpaterol or a salt thereof. The catalyst used in the reaction comprises metal complex of a ligand with a metal from transition group VIII. One such ligand used is ligand of Formula A.

These highly useful bidentate ligands of Formula A can be prepared by the process disclosed in US 2006/0089469. Schematic diagram of the process is shown below in Scheme I.

Scheme I

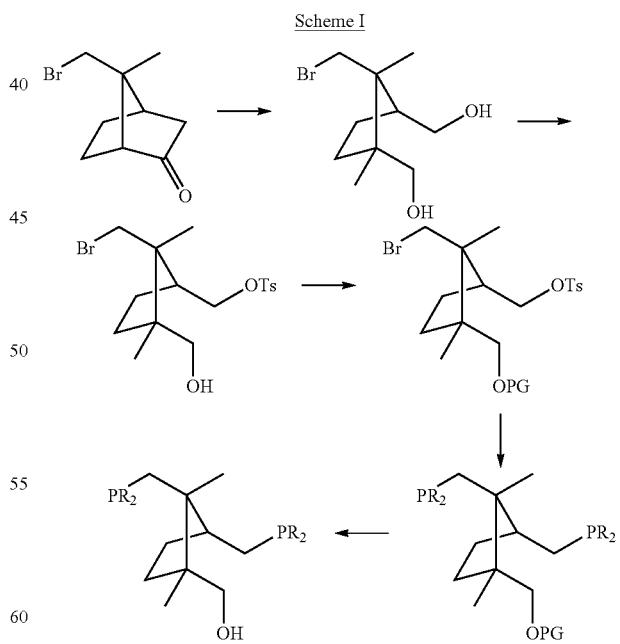

In the above reaction scheme, the group OPG- represents a hydroxyl protecting group. Komarov et al. in Tetrahedron Asymmetry, 13 (2002), 1615-1620 have disclosed a scheme to prepare the said ligand. Scheme II represents the scheme to prepare the said hydroxyphosphine ligand.

Scheme II

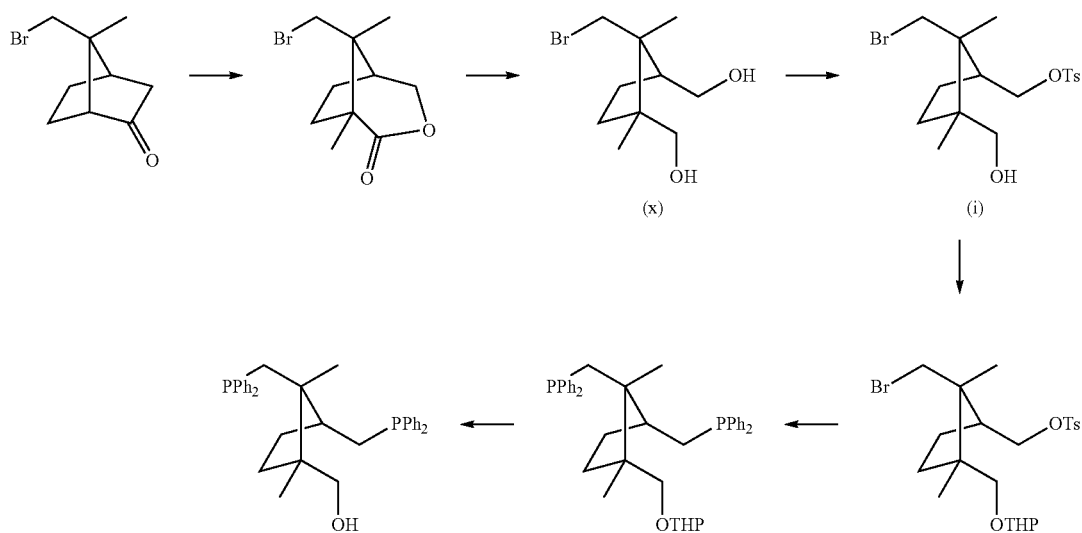

Inventors of the present invention, in an effort to prepare the hydroxyphosphine ligand of Formula A, tried to follow the process mentioned above. However, even after a series of experiments, the desired ligand could not be prepared in desired and reported yield. In fact, the yield was always negligible and the results were not reproducible. Working in a persuasive manner, the inventors of the present invention prepared novel intermediates which can be easily and conveniently converted into hydroxyphosphine ligands having application as mentioned above.

Accordingly, the present invention provides novel intermediates of Formula I useful in the preparation of hydroxyphosphine ligands useful in metal catalyzed asymmetric synthesis.

Further, according to the authors of Komarov et al. and US'469, the diol intermediate is selectively protected by converting it into tosylate (i). The publication also mentions that the more hindered hydroxyl group had to be protected before it could be reacted with lithium diphenylphosphine to avoid undesired cyclization.

Both the prior art references mentioned above use the route which involves selective protection of the less hindered alcohol group to get intermediate (i) which is difficult to handle as it has a tendency to undergo cyclization to form the compound (ii). Formation of compound (i) is very tricky as it is already known that while trying to form monotosylate (i) from the diol (x), the ditosylate (iii) also forms (Advances in catalysis, vol. 25, p 81-124, 1976). The monotosylate (i) and the ditosylate (ii) have to be separated by column chromatography. According to the reference, the monotosylate is used immediately after separation.

(ii)

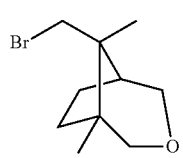

-continued (iii)

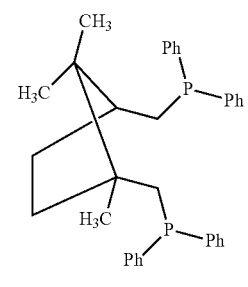

Formation of compound (i) is carried out under dry conditions, and uses large volume of pyridine as a solvent, which is carcinogenic, and is not an environmentally friendly solvent. Pyridine also makes the process less cost effective. Since it is soluble in water, its recovery is very difficult and need extra efforts. The reference does not mention any usefulness of the compound (ii), and is an unwanted product for the process.

Asymmetric homogenous hydrogenation, J D Morrison, W F Masler, M K Neuberg, Advances in Catalysis, Vol 25, pp. 81-124, [1976], also discloses a survey of asymmetric homogenous hydrogenation reactions, that is reactions that create asymmetric carbon atoms by the addition of hydrogen across multiple bonds under the influence of soluble chiral catalysts. This publication teaches a process for the preparation of Camphos from commercially available (+)-camphoric acid.

(+)-CAMPHOS

In the paragraph bridging pages 98-99, this publication teaches that in the initial trials to synthesize camphos, many procedures were used in an attempt to prepare dihalide from the diol. However, none of a great many standard methods met with any success. The procedures tried involved thionyl chloride, pyridine, phosphorus pentachloride and triphenylphosphine dibromide in N,N-dimethylformamide, triphenylphosphine and carbon tetrachloride, tris(dimethylamino)phosphine and bromine, o-phenylenephosphorochloridite and bromine, tris(dimethylamino)phosphine and carbon tetrachloride and tri-n-octylphosphine and carbon tetrachloride. This publication further states in the last paragraph on page 99 that the synthesis of camphos by displacement on its ditosylate precursor with the diphenylphosphide anion appeared promising on paper, but initially was a dismal failure in practice. It was considered likely that the less hindered α-tosylate group was displaced or eliminated rather readily at room temperature but the neopentyl-like-β-tosylate group required more strenuous conditions to effect its displacement. This was also found to reduce the yield of the target hydroxydiphosphine ligand, which is clearly undesirable.

Accordingly, there is a need in the art for a process for the preparation of a compound of formula A conveniently, in high yield and preferably, without utilizing an intermediate compound having a tosylate leaving group.

In fact, attempts to prepare the desired compound of formula A using the conventionally known process led to the undesired yield of an oxidized product only instead of the desired compound of formula A, having the formula set out below:

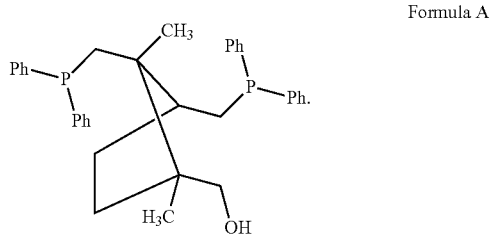 [SMILES: CC1(CO)CCC(CP(c2ccccc2)c2ccccc2)C1(C)CP(c1ccccc1)c1ccccc1]

Formula A

Inventors of the present invention, in an effort to prepare the hydroxyphosphine ligand of Formula A, tried to follow the process mentioned above. However, even after a series of experiments, they could not form (i) in desired and reported yield. In fact, the yield was always negligible and the results were not reproducible. Working in a persuasive manner, the inventors accidently found that the compound (ii) which was considered to be unwanted product by the prior art reference, can be conveniently and effectively converted into the desired hydroxydiphosphine ligand of Formula A.

Thus, there is a need in the art for a process for preparing hydroxydiphosphine ligands in high yield. These hydroxydiphosphine ligands are suitable precatalysts for the enantioselective manufacture of optically active agrochemicals, particularly chloroacetanilide herbicides. The process of the present invention is cost effective, environmentally friendly, simple, and reproducible.

OBJECTS OF THE INVENTION

An object of the present invention is to provide chiral intermediates which are useful in the preparation of hydroxyphosphine ligands.

Another object of the present invention is to provide intermediates that are useful for the preparation of hydroxyphosphine ligands which are used as ligands on transition metals in asymmetric metal catalyzed reactions.

Another object of the present invention is to provide intermediates for the preparation of [(1R,2R,3S)-1,2-dimethyl-2,3-bis(diphenyl phosphine methyl)cyclopentyl]methanol.

Another object of the present invention is to provide intermediates which lead to a convenient synthesis of chiral hydroxydiphosphine ligands in high yield.

Another object of the present invention is to provide a process for the preparation of chiral hydroxydiarylphosphine ligands.

Another object of the present invention is to provide a convenient process for the preparation of chiral hydroxydiarylphosphine ligands in high yield.

Another object of the present invention is to provide a process for the preparation of chiral hydroxydiarylphosphine ligands wherein the process does not lead to the formation of oxidized and other impurities.

Yet another object of the present invention is to provide a convenient process for the preparation of (1R,2R,3S)-1,2-dimethyl-2,3-bis(diphenyl phosphine methyl)cyclopentyl]methanol in high yield.

These and other objects of the invention are realized by an invention set out immediately hereinafter.

SUMMARY OF THE INVENTION

In one aspect, the present invention provides a compound of formula:

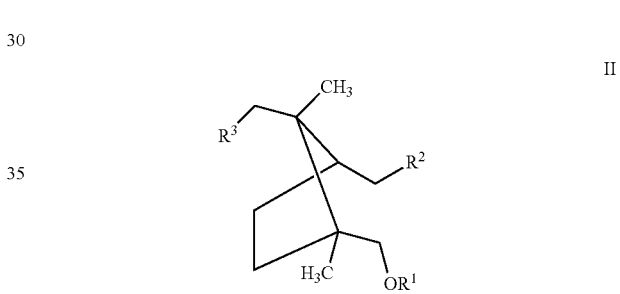

II wherein:
$R^1$ is hydrogen or a hydroxyl protecting group; and
$R^2$ and $R^3$ are same or different and are independently selected from halogen or —O—SO$_2$—X; wherein X is $C_1$-$C_4$ alkyl; $C_1$-$C_4$ alkyl substituted with one or more halogen; or substituted or unsubstituted phenyl wherein said phenyl substituent is selected from halogen, nitro and $C_1$-$C_4$ alkyl; provided that when $R^3$ is bromine, X is not p-toluoyl.

In another aspect, the present invention provides a compound of formula:

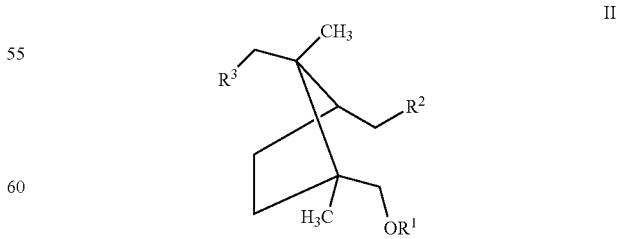

II wherein:
$R^1$ is hydrogen, Z or —SO$_2$—X;
$R^2$ and $R^3$ are same or different and are independently selected from halogen or —O—SO$_2$—X; wherein X is $C_1$-$C_4$ alkyl; $C_1$-$C_4$ alkyl substituted with one or more halogen; or substituted or unsubstituted phenyl wherein said phenyl substituent is selected from halogen, nitro and $C_1$-$C_4$ alkyl; and Z is a hydroxyl protecting group selected from the group comprising (tetrahydro-2H-pyran-2-yl); (tetrahydro-2H-pyran-2-one-3-yl); tetrahydro-2H-pyran-2-alkoxy-6-yl) wherein said "alkoxy" includes $C_1$-$C_4$ alkyloxy; triarylmethyl, wherein said aryl is preferably phenyl unsubstituted or substituted with one or more substituents selected from halogen, nitro, —O—$C_1$-$C_4$ alkyl and $C_1$-$C_4$ alkyl; 1,1,1,3,3,3-hexafluoro-2-aryl-isopropyl, wherein aryl is defined as above;

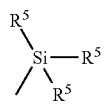

wherein $R_5$ may be same or different, and are independently selected from Ar or $C_1$-$C_4$ alkyl, wherein aryl group is as defined above; p-methoxy-benzyl; —(CH)$_n$($R_6$)-A-(CH$_2$)$_n$—W, wherein $R_6$ is hydrogen or $C_1$-$C_4$ alkyl, A is —O— or —S—, n is from 0 to 5, W is selected from hydrogen, $C_1$-$C_4$ alkyl, —O—($C_1$-$C_4$ alkyl) and aryl, said aryl being preferably a phenyl ring, unsubstituted or substituted with one or more substituents selected from halogen, nitro and $C_1$-$C_4$ alkyl; —(CH)$_n$($R_6$)—Ar, wherein n is as defined above and aryl is a phenyl ring, unsubstituted or substituted with one or more substituents selected from halogen, nitro and $C_1$-$C_4$ alkyl; 9-phenylxanthyl; and —C(=O)—$R_7$, wherein $R_7$ is selected from C1-C4 alkyl, halogenated C1-C4 alkyl and aryl, said aryl is a phenyl ring, unsubstituted or substituted with one or more substituents selected from halogen, nitro and $C_1$-$C_4$ alkyl, provided that when $R^3$ is bromine, $R^2$ may be —O—SO$_2$—X with the proviso that X is not p-toluoyl.

In yet another aspect, the present invention provides a compound of the formula:

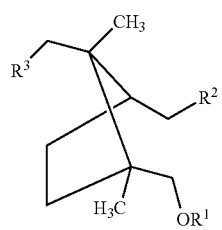

wherein:

$R^1$ is hydrogen or Z;

$R^2$ and $R^3$ are same or different and are independently selected from F, Cl, Br, I;

Z is a hydroxyl protecting group selected from tetrahydro-2H-pyran-2-yl; tetrahydro-2H-pyran-2-one-3-yl; tetrahydro-2H-pyran-2-methoxy-6-yl; and tetrahydro-2H-pyran-2-ethoxy-6-yl.

In another aspect, the present invention provides a compound of formula:

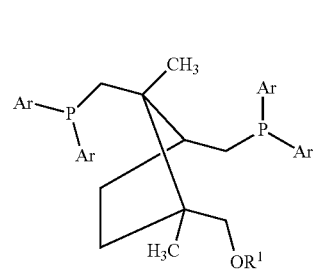

I wherein:

Ar is an aryl group, unsubstituted or substituted with one or more substituents independently selected from the group comprising $C_1$-$C_4$ alkyl, $C_1$-$C_4$ alkoxy, ($C_1$-$C_4$ alkyl)-amino, di-($C_1$-$C_4$ alkyl)-amino, nitro and $C_1$-$C_4$ alkyl substituted with one or more halogen;

$R^1$ is Z or —SO$_2$—X;

wherein X is $C_1$-$C_4$ alkyl; $C_1$-$C_4$ alkyl substituted with one or more halogen; or substituted or unsubstituted phenyl wherein said phenyl substituent is selected from halogen, nitro and $C_1$-$C_4$ alkyl; and Z is a hydroxyl protecting group selected from tetrahydro-2H-pyran-2-yl; tetrahydro-2H-pyran-2-one-3-yl; tetrahydro-2H-pyran-2-methoxy-6-yl; and tetrahydro-2H-pyran-2-ethoxy-6-yl.

In another aspect, the present invention provides a process for the preparation of a compound of formula:

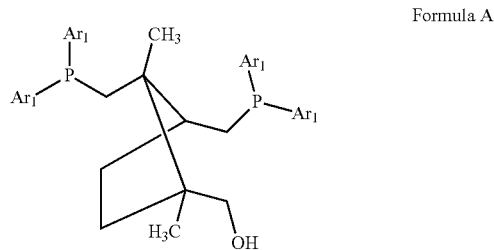

Formula A comprising deprotecting a compound of formula I:

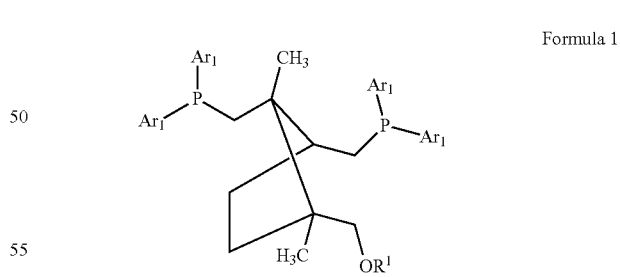

Formula 1 wherein:

$Ar_1$ is an aryl group, unsubstituted or substituted with one or more substituents independently selected from the group comprising $C_1$-$C_4$ alkyl, $C_1$-$C_4$ alkoxy, ($C_1$-$C_4$ alkyl-amino, di-($C_1$-$C_4$ alkyl)-amino, nitro and $C_1$-$C_4$ alkyl substituted with one or more halogen; and $R^1$ is a hydroxyl protecting group.

In another aspect, the present invention provides a process for the preparation of a compound of formula A

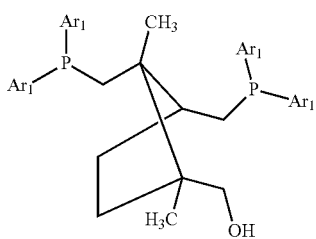

Formula A comprising:

(a) reducing a compound of formula V:

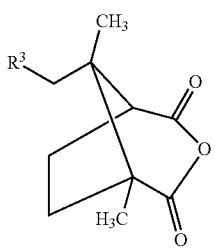

Formula V with a reducing agent to obtain a compound of formula VI:

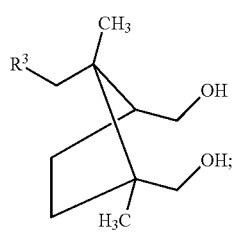

Formula VI (b) dehydrating said compound in the presence of a dehydrating agent to a compound of formula IV:

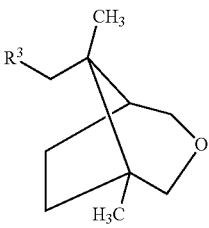

Formula IV (c) hydro-halogenating or hydro-sulfonating a compound of formula:

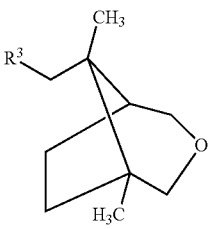

Formula IV to obtain a compound of formula III:

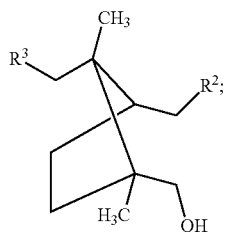

Formula III (d) protecting the hydroxyl group of the compound of formula III:

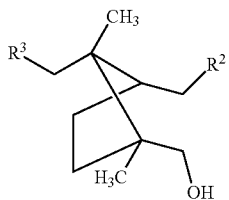

Formula III to obtain a compound of formula II:

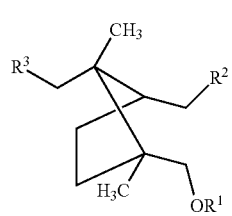

Formula II (e) reacting the compound of formula II

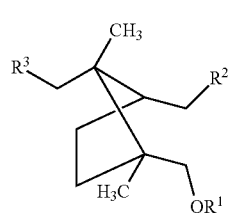

Formula II with an alkali metal salt of diphenylphosphine in an organic solvent; and (f) deprotecting the protected hydroxyl group to obtain a compound of formula:

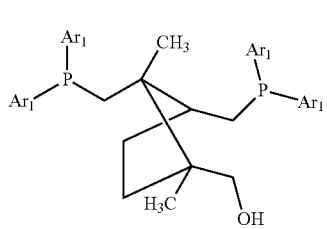

Formula A wherein:
Ar$_1$ is an aryl group, unsubstituted or substituted with one or more substituents independently selected from the group comprising C$_1$-C$_4$ alkyl, C$_1$-C$_4$ alkoxy, (C$_1$-C$_4$ alkyl)-amino, di-(C$_1$-C$_4$ alkyl)-amino, nitro and C$_1$-C$_4$ alkyl substituted with one or more halogen;
R$^1$ is a hydroxyl protecting group; and
R$^2$ and R$^3$ are same or different, each being independently selected from halogen or —SO$_2$—X, wherein X is C$_1$-C$_4$ alkyl, C$_1$-C$_4$ alkyl substituted with one or more halogen, or substituted or unsubstituted phenyl wherein said phenyl substituent is selected from halogen, nitro and C$_2$-C$_4$ alkyl.

DETAILED DESCRIPTION OF THE INVENTION

The present inventors have surprisingly found that the compounds of formula II are excellent precursors for the preparation of hydroxyphosphine ligands and enable their convenient preparation in an unexpectedly high yield and purity. Without wishing to be bound by theory, it is believed that the substituents R$^2$ and R$^3$ are capable of being conveniently displaced by diarylphosphine groups upon reaction with an alkali metal salt of diarylphosphide in an organic solvent, in contrast to p-toluenesulfonate group known in the art. The p-toluenesulfonate group was found to be a bad leaving group, which reduced the yield of the target hydroxyphosphine ligands. Surprisingly, the compounds of the present invention enable the preparation of hydroxyphosphine ligands conveniently and in high yield.

Accordingly, in one aspect, the present invention provides a compound of formula:

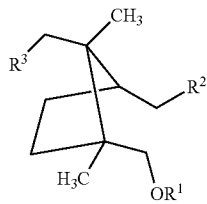

II wherein:
R$^1$ is hydrogen or a hydroxyl protecting group; and
R$^2$ and R$^3$ are same or different and are independently selected from halogen or —O—SO$_2$—X, wherein X is C$_1$-C$_4$ alkyl, C$_1$-C$_4$ alkyl substituted with one or more halogen, or substituted or unsubstituted phenyl wherein said phenyl substituent is selected from halogen, nitro and C$_1$-C$_4$ alkyl;
provided that when R$^3$ is bromine, X is not p-toluoyl.
In a preferred embodiment, R$^3$ is halogen.

The choice of a particular hydroxyl protecting group as a R$^1$ substituent is not particularly limiting. Generally, R$^1$ may be any group that may be conveniently employed to protect the hydroxyl group from taking part in a certain step of any organic synthesis. Preferably, the preferred R$^1$ substituent should be capable of being easily reconverted to the original hydroxyl group.

The choice of the R$^2$ and/or R$^3$ substituent is essential for the intermediates of the present invention to be convenient precursors for the chiral hydroxydiphosphine ligands.

In one embodiment, R$^2$ and R$^3$ may be same or different. Preferably, R$^2$ or R$^3$ is halogen or —O—SO$_2$—X, wherein X is C$_1$-C$_4$ alkyl; C$_1$-C$_4$ alkyl substituted with one or more halogen; or substituted or unsubstituted phenyl wherein said phenyl substituent is selected from halogen, nitro and C$_1$-C$_4$ alkyl.

In this aspect, the preferred substituent R$^3$ is a halogen.

In an embodiment, the hydroxyl protecting group may be selected from the substituent group —Z or —SO$_2$—X. Accordingly, R$^1$ may be selected from hydrogen, Z and —SO$_2$—X. In this embodiment, X may be selected from C$_1$-C$_4$ alkyl, C$_1$-C$_4$ alkyl substituted with one or more halogen, or substituted or unsubstituted phenyl wherein said phenyl substituent is selected from halogen, nitro and C$_1$-C$_4$ alkyl.

In this embodiment, Z may be selected from tetrahydro-2H-pyran-2-yl; tetrahydro-2H-pyran-2-one-3-yl; tetrahydro-2H-pyran-2-alkoxy-6-yl, wherein said "alkoxy" includes C$_1$-C$_4$ alkyloxy; triarylmethyl-, wherein said aryl is preferably phenyl ring, unsubstituted or substituted with one or more substituents selected from halogen, nitro, —O—C$_1$-C$_4$ alkyl and C$_1$-C$_4$ alkyl; 1,1,1,3,3,3-hexafluoro-2-aryl-isopropyl, wherein aryl is defined as above;

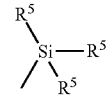

wherein R$_5$ may be same or different and are selected from Ar or C$_1$-C$_4$ alkyl, wherein aryl group is as defined above; p-methoxy-benzyl; —(CH)$_n$(R$_6$)-A-(CH$_2$)$_n$—W, wherein R$_6$ is hydrogen or C$_1$-C$_4$ alkyl, A is —O— or —S—, n is from 0 to 5, W is selected from hydrogen, C$_1$-C$_4$ alkyl, —O—(C$_1$-C$_4$ alkyl) and aryl, said aryl being preferably a phenyl ring, unsubstituted or substituted with one or more substituents selected from halogen, nitro and C$_1$-C$_4$ alkyl; —(CH)$_n$(R$_6$)—Ar, wherein n is as defined above and aryl is a phenyl ring, unsubstituted or substituted with one or more substituents selected from halogen, nitro and C$_1$-C$_4$ alkyl; 9-phenylxanthyl; and —C(=O)—R$_7$, wherein R7 is selected from C1-C4 alkyl, halogenated C1-C4 alkyl and aryl, said aryl is a phenyl ring, unsubstituted or substituted with one or more substituents selected from halogen, nitro and C$_1$-C$_4$ alkyl.

In this embodiment, R$^2$ may be preferably selected from halogen or —SO$_2$—X, wherein X is as defined above. Further, according to this embodiment, R$^3$ is preferably halogen. However, compounds are excluded from the scope of the present invention wherein R$^3$ is bromine and X is p-toluoyl group.

Thus, in this aspect, the present invention provides a compound of formula:

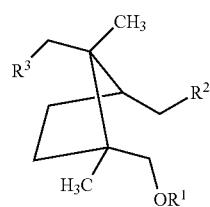

II wherein:
R$^1$ is hydrogen, Z or —SO$_2$—X;
R$^2$ and R$^3$ are same or different and are independently selected from halogen or —O—SO$_2$—X.

In this embodiment, X is $C_1$-$C_4$ alkyl, $C_1$-$C_4$ alkyl substituted with one or more halogen, or substituted or unsubstituted phenyl wherein said phenyl substituent is selected from halogen, nitro and $C_1$-$C_4$ alkyl.

In another embodiment, Z may be a hydroxyl protecting group selected from tetrahydro-2H-pyran-2-yl; tetrahydro-2H-pyran-2-one-3-yl; tetrahydro-2H-pyran-2-alkoxy-6-yl, wherein said "alkoxy" includes $C_1$-$C_4$ alkyloxy; triarylmethyl-, wherein said aryl is preferably phenyl ring, unsubstituted or substituted with one or more substituents selected from halogen, nitro, —O—$C_1$-$C_4$ alkyl and $C_1$-$C_4$ alkyl; 1,1,1,3,3,3-hexafluoro-2-aryl-isopropyl, wherein aryl is defined as above;

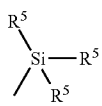

wherein $R_5$ may be same or different and are selected from Ar or $C_1$-$C_4$ alkyl, wherein aryl group is as defined above; p-methoxy-benzyl; —$(CH)_n(R_6)$-A-$(CH_2)_n$—W, wherein $R_6$ is hydrogen or $C_1$-$C_4$ alkyl, A is —O— or —S—, n is from 0 to 5, W is selected from hydrogen, $C_1$-$C_4$ alkyl, —O—($C_1$-$C_4$ alkyl) and aryl, said aryl being preferably a phenyl ring, unsubstituted or substituted with one or more substituents selected from halogen, nitro and $C_1$-$C_4$ alkyl; —$(CH)_n(R_6)$—Ar, wherein n is as defined above and aryl is a phenyl ring, unsubstituted or substituted with one or more substituents selected from halogen, nitro and $C_1$-$C_4$ alkyl; 9-phenylxanthyl; and —C(=O)—$R_7$, wherein $R_7$ is selected from C1-C4 alkyl, halogenated C1-C4 alkyl and aryl, said aryl is a phenyl ring, unsubstituted or substituted with one or more substituents selected from halogen, nitro and $C_1$-$C_4$ alkyl.

In a further preferred embodiment, X is selected from methyl; trifluoromethyl; n-novafluorobutyl; 2,2,2-trifluoroethyl; p-toluoyl; p-nitrophenyl or p-bromophenyl. However, in this embodiment, when $R^3$ is bromo-, X does not include p-toluoyl when appearing in the $R^2$ substituent.

In this embodiment, Z may be preferably selected from tetrahydro-2H-pyran-2-yl; tetrahydro-2H-pyran-2-one-3-yl; tetrahydro-2H-pyran-2-methoxy-6-yl; tetrahydro-2H-pyran-2-ethoxy-6-yl; triphenylmethyl-, wherein one or more of the phenyl rings are optionally substituted with p-methoxy group; 1,1,1,3,3,3-hexafluoro-2-phenylisopropyl), wherein said phenyl ring may be optionally substituted with p-methoxy group;

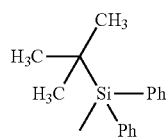

wherein the phenyl groups may be optionally substituted with halogen, nitro, $C_1$-$C_4$ alkyl or $C_1$-$C_4$ alkoxy; p-methoxy-benzyl; $CH_2OCH_3$; $CH_2OCH_2CH_2OCH_3$; —$CH_2SCH_3$; —$CH_2SCH_2$-Ph; —$CH(CH_3)$—O—$CH_2CH_3$; —$CH_2$Ph; —$CH_2$-o-nitrophenyl; —$CH_2$-p-methoxyphenyl; -9-phenylxanthyl; —$Si(Me)_3$; —$Si(Et)_3$; —$Si(i-Pr)_3$; —$Si(Ph)Me_2$; —$Si(t-Bu)Me_2$; —$Si(t-Bu)Ph_2$; —$C(O)CF_3$; —$C(O)(t-Bu)$; and —$C(O)$ Ph.

Accordingly, in this embodiment, the present invention provides a compound of the formula:

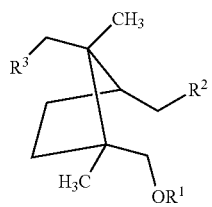

wherein:
$R^1$ is hydrogen, Z or —$SO_2$—X;
$R^2$ and $R^3$ are same or different and each may be independently selected from F, Cl, Br, I or —O—$SO_2$—X, with the proviso that when $R^3$ is bromine, $R^2$ is not p-toluenesulfonate; X is methyl, trifluoromethyl, n-novafluorobutyl, 2,2,2-trifluoroethyl, p-toluoyl, p-nitrophenyl or p-bromophenyl; and Z is a hydroxyl protecting group selected from tetrahydro-2H-pyran-2-yl; tetrahydro-2H-pyran-2-one-3-yl; tetrahydro-2H-pyran-2-methoxy-6-yl; tetrahydro-2H-pyran-2-ethoxy-6-yl; triphenylmethyl-, wherein one or more of the phenyl rings are optionally substituted with p-methoxy group; 1,1,1,3,3,3-hexafluoro-2-phenylisopropyl), wherein said phenyl ring may be optionally substituted with p-methoxy group;

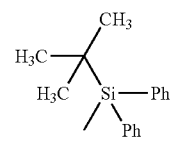

wherein the phenyl groups may be optionally substituted with halogen, nitro, $C_1$-$C_4$ alkyl or $C_1$-$C_4$ alkoxy; p-methoxy-benzyl; —$CH_2OCH_3$; —$CH_2OCH_2CH_2OCH_3$; —$CH_2SCH_3$; —$CH_2SCH_2$-Ph; —$CH(CH_3)$—O—$CH_2CH_3$; —$CH_2$Ph; —$CH_2$-o-nitrophenyl; —$CH_2$-p-methoxyphenyl; -9-phenylxanthyl; —$Si(Me)_3$; —$Si(Et)_3$; —$Si(i-Pr)_3$; —$Si(Ph)Me_2$; —$Si(t-Bu)Me_2$; —$Si(t-Bu)Ph_2$; —$C(O)CF_3$; —$C(O)(t-Bu)$; and —$C(O)Ph$.

Still more preferably, $R^1$ is Z or hydrogen. In this or other preferred embodiments, $R^2$ and $R^3$, may be same or different, each independently selected from F, Cl, Br or I.

Still more preferably, the hydroxyl protecting group may be selected from tetrahydro-2H-pyran-2-yl, tetrahydro-2H-pyran-2-one-3-yl, tetrahydro-2H-pyran-2-methoxy-6-yl, and tetrahydro-2H-pyran-2-ethoxy-6-yl.

Accordingly, in this preferred embodiment, the present invention provides a compound of formula:

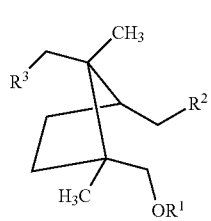

wherein:
$R^1$ is hydrogen or Z;
$R^2$ is F, Cl, Br, I;
$R^3$ is F, Cl, Br or I;

Z is a hydroxyl protecting group selected from tetrahydro-2H-pyran-2-yl, tetrahydro-2H-pyran-2-one-3-yl, tetrahydro-2H-pyran-2-methoxy-6-yl, and tetrahydro-2H-pyran-2-ethoxy-6-yl.

The compounds of formula II according to the present invention are suitable intermediates for the preparation of hydroxyphosphine ligands, which are convenient co-catalytic ligands for the enantioselective preparation of compounds of pharmaceutical and agrochemical relevance. The compounds of formula III may themselves be prepared from the bicyclic ether compounds disclosed in Komarov et al., which is incorporated herein in its entirety.

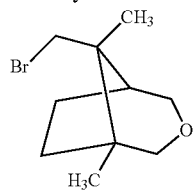

For example, when $R^2$ is a halogen, it may be prepared using the following reaction scheme:

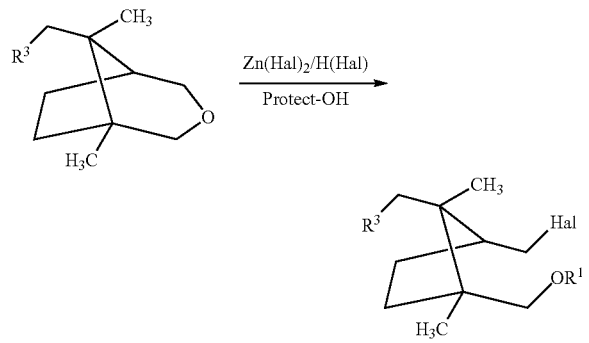

As aforesaid, the compounds of formula II are suitable intermediates for the preparation of hydroxyphosphine ligands, which are convenient co-catalytic ligands for the enantioselective preparation of compounds of pharmaceutical and agrochemical relevance. These compounds are conveniently reacted with an alkali metal salt of an diarylphosphide to obtain further intermediate compounds of formula I, which are capable of being directly deprotected to the target hydroxyphosphine ligands. These compounds of formula I are themselves new and also form an aspect of the present invention.

Thus, in this aspect, the present invention provides a compound of formula:

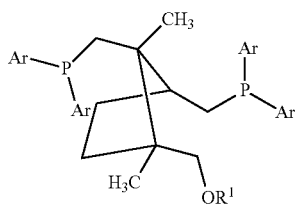

I wherein:
Ar is an aryl group, unsubstituted or substituted with one or more substituents independently selected from the group comprising $C_1$-$C_4$ alkyl, $C_1$-$C_4$ methoxy, ($C_1$-$C_4$ alkyl)-amino, di-($C_1$-$C_4$ alkyl)-amino, nitro and $C_1$-$C_4$ alkyl substituted with one or more halogen; and
$R^1$ is a hydroxyl protecting group being Z or —SO$_2$—X;

wherein X is $C_1$-$C_4$ alkyl, $C_1$-$C_4$ alkyl substituted with one or more halogen, or substituted or unsubstituted phenyl wherein said phenyl substituent is selected from halogen, nitro and $C_1$-$C_4$ alkyl; and
Z is a hydroxyl protecting group selected from tetrahydro-2H-pyran-2-yl; tetrahydro-2H-pyran-2-one-3-yl; tetrahydro-2H-pyran-2-methoxy-6-yl; and tetrahydro-2H-pyran-2-ethoxy-6-yl.

The deprotection of the masked hydroxyl group, according to the present invention, is not particularly limiting and may be carried out as conventionally practiced by a skilled organic chemist for the particular protecting group. For example, reference is drawn to Carey & Sundberg, Chapter 13.1, which discusses the deprotection reactions of hydroxyl protecting groups. Such reactions according to the present invention may be carried out using processes described herein, all of which are incorporated herein by reference.

The compounds of the present invention can be obtained in a wide range of substituent variations. These variations can also alter the steric and electronic properties of the resultant compound so as to enable their selectivity and activity in homogenously catalyzed process to be controlled.

In another aspect, aspect, the present invention provides a process for the preparation of a compound of formula A:

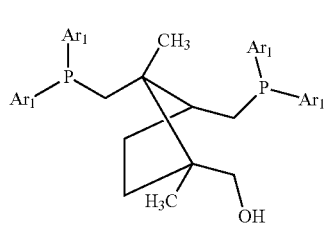

Formula A comprising deprotecting a compound of formula I:

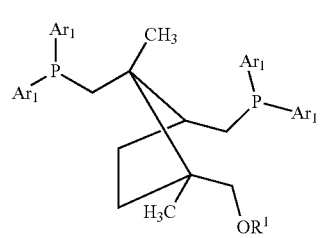

Formula I wherein $R^1$ is a hydroxyl protecting group; and
$Ar_1$ is an aryl group, unsubstituted or substituted with one or more substituents independently selected from the group comprising $C_1$-$C_4$ alkyl, $C_1$-$C_4$ alkoxy, ($C_1$-$C_4$ alkyl)-amino, di-($C_1$-$C_4$ alkyl)-amino, nitro and $C_1$-$C_4$ alkyl substituted with one or more halogen.

In a preferred embodiment, each $Ar_1$ group may be same or different, and each may be independently selected from phenyl, 4-methylphenyl, 3,5-dimethylphenyl, 3,5-diisopropylphenyl, 4-methoxyphenyl, 4-methoxy-3,4-dimethylphenyl, 3,5-di-t-butylphenyl, 4-methylamino-3,5-t-butylphenyl, 4-trifluoromethylphenyl and 3,5-difluoromethylphenyl.

In a most preferred embodiment, each $Ar_1$ group is phenyl.

The term "hydroxyl protecting group" as used herein denotes a protective group introduced into the compounds and intermediates of the present invention by reaction with the hydroxyl group in order to obtain chemoselectivity in a subsequent chemical reaction. In this invention, the term "hydroxyl protecting group" additionally means the substituents included within the definition of $R^1$ specified in any aspect or embodiment hereinafter. The masking of a hydroxyl group in the compounds and intermediates of the present invention prevents the protected hydroxyl group from itself taking part in the reaction and is capable of being easily removed from the masking position once the desired reaction is over.

There are several hydroxyl protecting groups known in the art, which all form a part of the present invention. Preferably, the reaction step of deprotecting a compound of formula II varies with the particular protecting group utilized to mask the hydroxyl group. The choice of the particular protecting group and the deprotection reactions convenient for the selected protecting group are known to a skilled chemist and do not form a critical part of the present invention.

In a preferred embodiment of this aspect of the invention, the hydroxyl protecting group is $R^1$, which may be selected from Z or —$SO_2$—X.

In an embodiment, X is selected from $C_1$-$C_4$ alkyl, $C_1$-$C_4$ alkyl substituted with one or more halogen, or unsubstituted or substituted phenyl wherein said substituent on phenyl ring is selected from halogen, nitro and $C_1$-$C_4$ alkyl. In this embodiment, Z is a hydroxyl protecting group selected from tetrahydro-2H-pyran-2-yl; tetrahydro-2H-pyran-2-one-3-yl; tetrahydro-2H-pyran-2-alkoxy-6-yl, wherein said "alkoxy" includes $C_1$-$C_4$ alkyl; triarylmethyl-, wherein said aryl is preferably phenyl ring, unsubstituted or substituted with one or more substituents selected from halogen, nitro, —O—$C_1$-$C_4$ alkyl and $C_1$-$C_4$ alkyl; 1,1,1,3,3,3-hexafluoro-2-aryl-isopropyl, wherein aryl is defined as above;

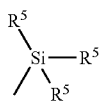

wherein $R_5$ may be same or different and are selected from Ar or $C_1$-$C_4$ alkyl, wherein aryl group is as defined above; p-methoxy-benzyl; $(CH)_n(R_6)$-A-$(CH_2)_n$—W, wherein $R_6$ is hydrogen or $C_1$-$C_4$ alkyl, A is —O— or —S—, n is from 0 to 5, W is selected from hydrogen, $C_1$-$C_4$ alkyl, —O—($C_1$-$C_4$ alkyl) and aryl, said aryl being preferably a phenyl ring, unsubstituted or substituted with one or more substituents selected from halogen, nitro and $C_1$-$C_4$ alkyl; —$(CH)_n(R_6)$—Ar, wherein n is as defined above and aryl is a phenyl ring, unsubstituted or substituted with one or more substituents selected from halogen, nitro and $C_1$-$C_4$ alkyl; 9-phenylxanthyl; and —C(=O)—$R_7$, wherein R7 is selected from C1-C4 alkyl, halogenated C1-C4 alkyl and aryl, said aryl is a phenyl ring, unsubstituted or substituted with one or more substituents selected from halogen, nitro and $C_1$-$C_4$ alkyl.

In a further preferred embodiment of any aspect described hereinabove, X may be selected from methyl; trifluoromethyl; n-novafluorobutyl; 2,2,2-trifluoroethyl; p-toluoyl; p-nitrophenyl and p-bromophenyl, while Z is a hydroxyl protecting group selected from tetrahydro-2H-pyran-2-yl; tetrahydro-2H-pyran-2-one-3-yl; tetrahydro-2H-pyran-2-methoxy-6-yl; tetrahydro-2H-pyran-2-ethoxy-6-yl; triphenylmethyl-, wherein one or more of the phenyl rings are optionally substituted with p-methoxy group; 1,1,1,3,3,3-hexafluoro-2-phenylisopropyl, wherein said phenyl ring may be optionally substituted with p-methoxy group;

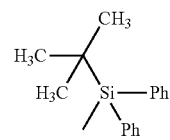

wherein the phenyl groups may be optionally substituted with halogen, nitro, $C_1$-$C_4$ alkyl or $C_1$-$C_4$ alkoxy; p-methoxy-benzyl; $CH_2OCH_3$; $CH_2OCH_2CH_2OCH_3$; —$CH_2SCH_3$; —$CH_2SCH_2$-Ph; —$CH(CH_3)$—O—$CH_2CH_3$; —$CH_2Ph$; —$CH_2$-o-nitrophenyl; —$CH_2$-p-methoxyphenyl; -9-phenylxanthyl; —Si(Me)$_3$; —Si(Et)$_3$; —Si(i-Pr)$_3$; —Si(Ph)Me$_2$; —Si(t-Bu)Me$_2$; —Si(t-Bu)Ph$_2$; —C(O)CF$_3$; —C(O)(t-Bu); and —C(O)Ph.

In a further preferred embodiment, Z is selected from tetrahydro-2H-pyran-2-yl; tetrahydro-2H-pyran-2-one-3-yl; tetrahydro-2H-pyran-2-methoxy-6-yl; and tetrahydro-2H-pyran-2-ethoxy-6-yl.

In a further preferred embodiment of any aspect described hereinabove, the protecting group suitable according to the present invention and the corresponding deprotection reactions are provided hereinbelow, all of which may be conveniently utilized in an embodiment of the present invention. Preferably, the hydroxyl protecting group may be selected so as to enable selective protection and deprotection for the hydroxyl group efficiently and must be inert to a reaction occurring at any other moiety of the compounds or intermediates occurring in the processes of the present invention.

| S No. | Protecting Group | Protection reaction conditions | Deprotection reaction conditions |
|---|---|---|---|
| 1 | Methoxymethyl ether (—OCH$_2$OMe) | MeOCH$_2$Cl, NaH in THF; MeOCH$_2$Cl in dichloromethane in the presence of i-Pr$_2$EtN | Me$_2$BBr$_2$ |
| 2 | Methoxyethoxymethyl ether (—OCH$_2$OCH$_2$CH$_2$OMe) | MeOCH$_2$CH$_2$OCH$_2$Cl in NaH and THF; MeOCH$_2$CH$_2$OCH$_2$Cl in dichloromethane in the presence of i-Pr$_2$EtN | ZnBr$_2$; TiCl$_4$; Me$_2$BBr$_2$. |
| 3 | Methyl thiomethyl ethers (—OCH$_2$SMe) | MeSCH$_2$Cl in NaH and THF | HgCl$_2$, CH$_3$CN/H$_2$O; AgNO$_3$, THF in aqueous basic conditions |

-continued

| S No. | Protecting Group | Protection reaction conditions | Deprotection reaction conditions |
|---|---|---|---|
| 4 | Benzyloxymethyl ethers (—OCH$_2$OCH$_2$Ph) | PhOCH$_2$CH$_2$Cl in dichloromethane in the presence of i-Pr$_2$EtN | Hydrogen in PtO$_2$; Na/NH$_3$ in ethanol |
| 5 | Tetrahydropyranyl ether (THP) | Dihydropyran in p-toluenesulfonic acid in benzene | Acetic acid in THF (aq.); Amberlyst H-15 in MeOH |
| 5 | Benzyl ether (—OCH$_2$Ph) | Benzyl chloride in KH/THF; PhCH$_2$OC(=NH)CCl$_3$ in F$_3$CSO$_3$H | H$_2$/PtO$_2$; Li/NH$_3$. |
| 6 | 2-Naphthylmethyl ether (NAP) | 2-chloromethyl naphthalene in KH | Hydrogenolysis H$_2$ in Pd/C |
| 7 | p-methoxybenzyl ethers | p-MeOPhCH2Cl in KH/THF; p-MeOPhCH$_2$O—C(=NH)CCl$_3$ in F$_3$CSO$_3$H | H$_2$/PtO$_2$; Li/NH$_3$; Ce(NH$_4$)$_2$(NO$_3$)$_6$ |
| 8 | o-Nitrobenzyl ether | o-Nitrobenzyl chloride in NaH/THF | Photolysis at 320 nm |
| 9 | p-Nitrobenzyl ether | p-Nitrobenzyl chloride in NaH/THF | DDQ; Hydrogenolysis H$_2$ in Pd/C |
| 10 | 9-phenylxanthyl | 9-phenylxanthyl chloride in pyridine | Photolysis at 300 nm in aq. Acetonitrile |
| 11 | Trityl ether (—OCPh$_3$) or 4'-methoxytrityl or 4',4'-dimethoxytrityl | Trityl chloride in pyridine in the presence of DMAP; Ph$_3$C$^+$BF$_4^-$ | Mild acid e.g. 80% aq. AcOH at 20° C. |
| 12 | Trimethyl silyl ether (Me$_3$SiO—) or triethylsilyl ether or tri-isopropylsilyl ether, phenyldimethylsilyl ether | R$^3$Si—Cl in pyridine and DMAP; R$^3$Si—Cl in dichloromethane, imidazole and DMAP; R$_3$Si—OTf in i-Pr$_2$EtN in dichloromethane | H$_2$O/AcOH/THF in ratio of (3:5:11) for 15 hours |
| 13 | t-butyldimethylsilyl ether (t-BuMe$_2$Si—OR) | t-butyldimethylsilyl triflate | Acid hydrolysis or F$^-$ from HF, KF, CsF or n-Bu$_4$NF |
| 14 | t-Butyldiphenyl silyl ether (t-BuPh$_2$Si—OR) | t-BuPh$_2$Si—Cl in pyridine and DMAP; t-BuPh$_2$Si—Cl in dichloromethane, imidazole and DMAP; t-BuPh$_2$Si—OTf in i-Pr$_2$EtN in dichloromethane | F$^-$ from n-Bu$_4$NF (basic conditions) or HF/H$_2$O/CH$_3$CN or HF•pyridine or SiF$_4$•CH$_2$Cl$_2$. |
| 15 | Acetates (—O$_2$CCH$_3$) | Acetic anhydride in pyridine or acetyl chloride in pyridine | K$_2$CO$_3$ in methanol under reflux or KCN in methanol under reflux or NH$_3$/MeOH, LiOH in THF/H$_2$O |
| 16 | Trifluoroacetates | Trifluoroacetic anhydride or trifluoroacetyl chloride | K$_2$CO$_3$ in MeOH |
| 17 | Pivaloate | t-butylacetyl chloride or t-butylacetic anhydride | Mild base |
| 18 | Benzoate | Benzoyl chloride or benzoic anhydride or benzoyl cyanide or benzoyl tetrazole | Mild base or KCN/MeOH under reflux |

The list tabulated above is exemplary and is not intended to be exhaustive. Further hydroxyl protecting groups and corresponding deprotection reactions including conditions maintained therein are discussed in *J. Chem. Soc., Perkin Trans.* 1, 1998, 4005-4037, which is incorporated herein by reference in its entirety.

It was surprising indeed that a compound of formula I herein could be easily deprotected to the desired compound of formula A in high yield. The present inventors have found that under the reaction conditions disclosed in Tetrahedron Asymmetry, 13 (2002), 1615-1620, this compound of formula A was not detected possibly due to this compound being exceedingly susceptible to oxidation. Accordingly, the yield of the target compound of formula A was found negligible in the process disclosed in Tetrahedron Asymmetry, 13 (2002), 1615-1620. In an embodiment, the compound of formula I is extracted and stored under Argon atmosphere to prevent its oxidation in contact with air.

In an embodiment, the compound of formula I:

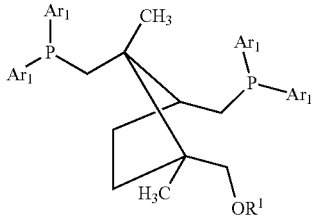

Formula I is prepared by the nucleophilic substitution of the leaving groups $R^2$ and $R^3$ present in a compound of formula II with an alkali metal salt of diaryl phosphine in an organic solvent.

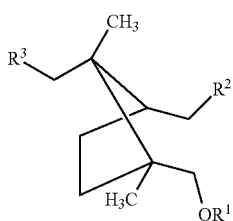

Formula II

Preferably, lithium salt of diphenylphosphine (LiPPh$_2$) may be used. It has been found that the leaving groups $R^2$ and $R^3$ are efficient leaving groups for the instant nucleophilic substitution in comparison to "tosylate" leaving group and thus lead to a surprisingly high yield of the target compound of formula A. Accordingly, in this aspect, the present invention provides a process for the preparation of a compound of formula

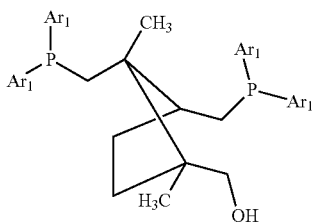

Formula A comprising:
(a) reacting a compound of formula II:

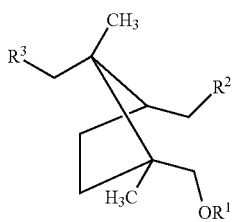

Formula II with an alkali metal salt of diphenylphosphine in an organic solvent; and optionally where $R^1$ is not hydrogen, (b) deprotecting the protected hydroxyl group to obtain a compound of formula A:

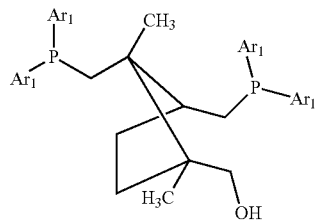

Formula A

In an embodiment, the preferred reagents useful for the introduction on the diaryl group may be thionyl chloride, pyridine, phosphorus pentachloride and triphenylphosphine dibromide in N,N-dimethylformamide; triphenylphosphine in carbon tetrachloride; tris(dimethylamino)phosphine and bromine; o-phenylenephosphorochloridite and bromine; tris (dimethylamino)phosphine and carbon tetrachloride and tri-n-octylphosphine and carbon tetrachloride. However, other synthetic routes that are known to a skilled organic chemist are not excluded and may be conveniently utilized according to an embodiment of the instant invention.

The substituent $R^2$ and $R^3$ may be same or different and each may be independently selected from halogen or —O—SO$_2$—X, wherein X is $C_1$-$C_4$ alkyl, $C_1$-$C_4$ alkyl substituted with one or more halogen, or substituted or unsubstituted phenyl wherein said phenyl substituent is selected from halogen, nitro and $C_2$-$C_4$ alkyl. However, where $R^3$ is bromine, X does not include p-toluoyl.

In another preferred embodiment, the preferred substituents $R^2$ and $R^3$ are halogen.

In a further preferred embodiment, $R^2$ and $R^3$ are selected from F, Cl, Br and I, and —O—SO$_2$—X, wherein X is selected from methyl, trifluoromethyl, n-novafluorobutyl, 2,2,2-trifluoroethyl, p-nitrophenyl or p-bromophenyl.

In a more preferred embodiment, both $R^2$ and $R_3$ are selected from F, Cl, Br and I.

In another aspect, the compound of formula II is obtained by protecting the hydroxyl group in a compound of formula III:

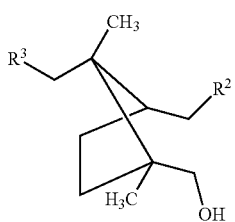

Formula III

The substituent groups $R^2$ and $R^3$ in this aspect of the present invention are as defined hereinabove in any/all aspects and embodiments. Preferably, the hydroxyl protecting group may be selected from the groups listed as in the above table so as to enable selective protection and deprotection for the hydroxyl group efficiently and must be inert to a reaction occurring at any other moiety of the compounds or intermediates occurring in the processes of the present invention.

The substituent $R^1$ may depend on the protecting group selected but may be defined according to any aspect or embodiment hereinabove. The choice of the particular protecting group and the deprotection reactions convenient for the selected protecting group are known to a skilled chemist and do not form a critical part of the present invention. Accordingly, in this aspect, the present invention provides a process for the preparation of a compound of formula

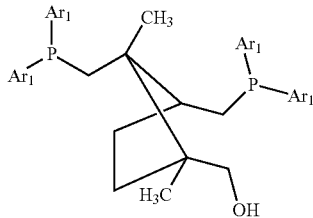

Formula A comprising:

(a) protecting the hydroxyl group of the compound of formula III:

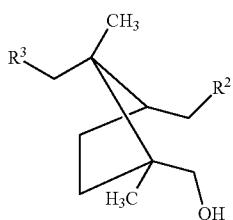

Formula III to obtain a compound of formula II:

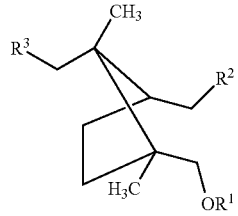

Formula II (b) reacting the compound of formula II

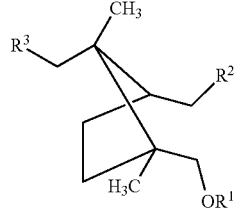

Formula II with an alkali metal salt of diarylphosphine in an organic solvent to obtain a compound of formula I; and (c) deprotecting the protected hydroxyl group to obtain a compound of formula:

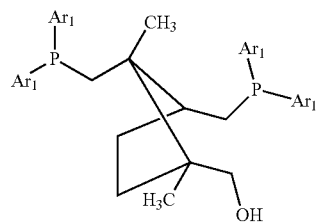

Formula A

The substituents $R^1$, $R^2$ and $R^3$ according to the instant aspect may be selected as per the definitions in any previous aspect or embodiment of the invention.

In yet another aspect, the compound of formula III:

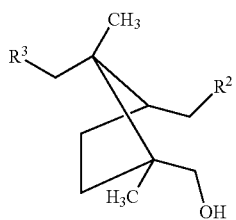

Formula III is obtained by hydro-halogenating or hydro-sulfonating an intermediate having the formula IV:

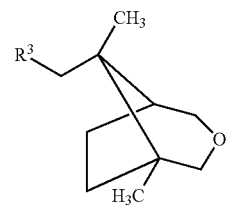

Formula IV

It was indeed surprising that hydro-halogenating the closed ring intermediate having the formula IV led exclusively to the formation of a product having hydroxyl group positioned at the less-hindered position, which led to a surprising increase in the yield of the final compound of formula A. This surprising chemoselectivity was observed more pronounced when both $R^2$ and $R^3$ were selected from F, Cl, Br and I in the presence of known halogenating reagents. In this embodiment, the choice of particular halogenating agent is not particularly critical and may be determined by a person skilled in the art.

In a preferred embodiment, the suitable halogenating agent may be selected from:

(a) Halogen in AcOH or $ClSO_3H$;
(b) $Zn(hal)_2$ in $H(hal)$;
(c) $B(hal)_3$ in $Ph_3P$; and
(d) $B(hal)_3$ in p-TsCl.

These halogenating agents are only to be construed as being exemplary and should not be considered exhaustive. A person skilled in the art may choose other halogenating agents that are known in the art. Thus, in this aspect, the present invention provides a process for the preparation of a compound of formula Formula A

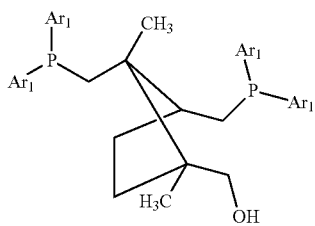

comprising:
(a) hydro-halogenating or hydro-sulfonating a compound of formula IV:

Formula IV

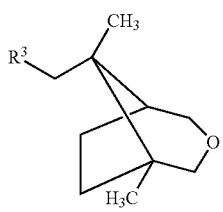

to obtain a compound of formula III:

Formula III

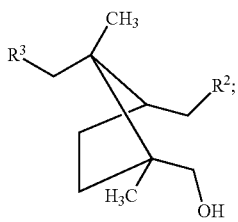

(b) protecting the hydroxyl group of the compound of formula III:

Formula III

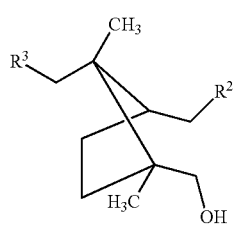

to obtain a compound of formula II:

Formula II

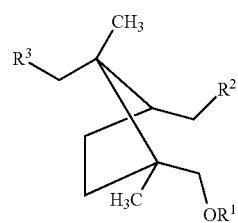

(c) reacting the compound of formula II

Formula II

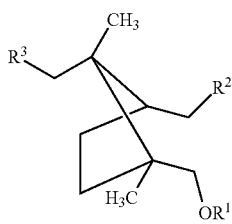

with an alkali metal salt of diarylphosphine in an organic solvent; and
(d) deprotecting the protected hydroxyl group to obtain a compound of formula:

Formula A

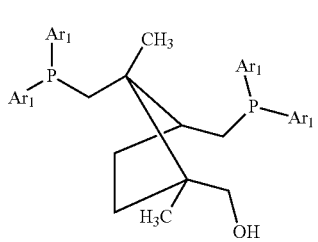

The definitions of the substituents $R^1$, $R^2$ and $R^3$ according to the instant aspect of the invention are as per the definitions provided in any previous aspect or embodiment thereof.

In another aspect, the closed ring compound of the formula IV:

Formula IV

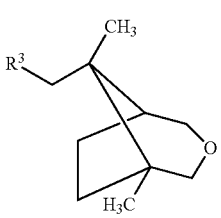

may be prepared as per the process disclosed in Tetrahedron Asymmetry, 13 (2002), 1615-1620, wherein the production of such a compound is described as an undesired by-product.

Alternatively, the said closed ring compound may be prepared by dehydrating a diol having the formula VI to obtain the resultant cyclic ether.

Formula VI

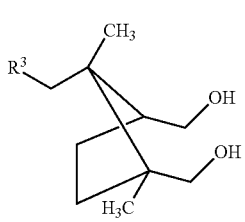

In another embodiment, the cyclic ether may be obtained by reducing a 9-substituted camphor derivative having the formula V to obtain a diol intermediate:

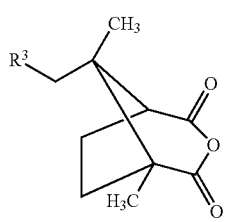

Formula V and subjecting the resultant diol to dehydration in the presence of a dehydrating agent to obtain said cyclic ether compound.

The reducing agent utilized in this step of the process is not particularly critical but may be any reducing agent typically used in organic synthesis to reduce ketones to alcohols. In a particular embodiment, the preferred reducing agent may be lithium aluminum hydride. In another embodiment, the reducing agent may be further selected from sodium borohydride and hydrogen with transition metal catalyst.

Preferably, the dehydrating agent may be selected from para-toluene sulfonyl chloride, zinc bromide in HBr and sulfuric acid although other dehydrating agents are not excluded.

Accordingly, in this aspect, the present invention provides a process for the preparation of a compound of formula

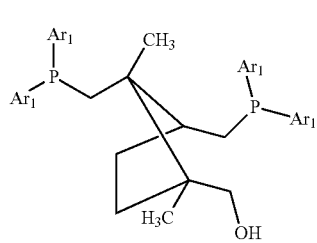

Formula A comprising:
(a) optionally reducing a compound of formula V:

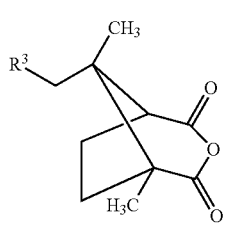

Formula V with a reducing agent to obtain a compound of formula VI:

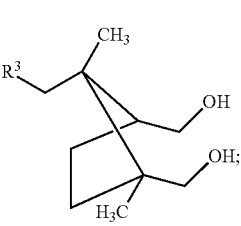

Formula VI (b) dehydrating said compound of formula VI in the presence of a dehydrating agent to a compound of formula IV:

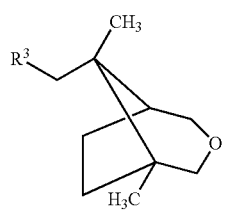

Formula IV (c) hydro-halogenating or hydro-sulfonating said compound of formula IV:

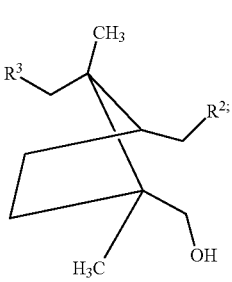

Formula IV to obtain a compound of formula III:

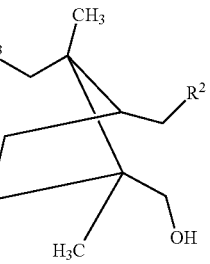

Formula III (d) protecting the hydroxyl group of the compound of formula III:

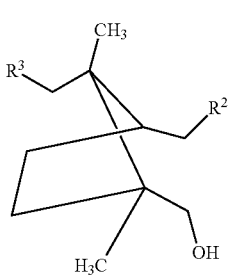

Formula III to obtain a compound of formula II:

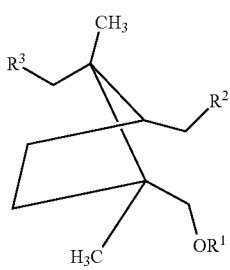

Formula II (e) reacting the compound of formula II

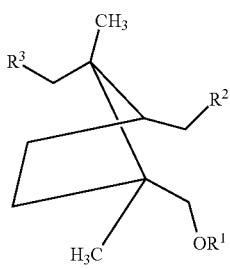

Formula II with an alkali metal salt of diarylphosphine in an organic solvent; and (f) deprotecting the protected hydroxyl group to obtain a compound of formula:

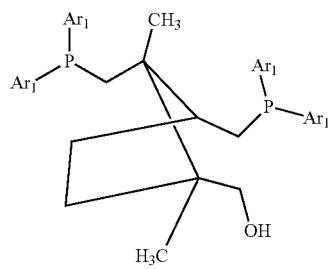

Formula A wherein $Ar_1$, $R^1$, $R^2$ and $R^3$ are as described in any aspect or embodiment hereinabove.

In another embodiment of this aspect, the intermediate diol formed from reducing the 9-substituted camphor derivative may not be separately extracted but in-situ formed diol may be subjected to dehydration under basic conditions to directly obtain the cyclic ether intermediate without separating the intermediate diol. Thus, in this embodiment, a compound having the formula IV:

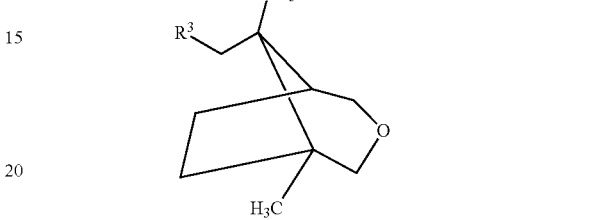

Formula IV is obtained by reducing a compound of formula:

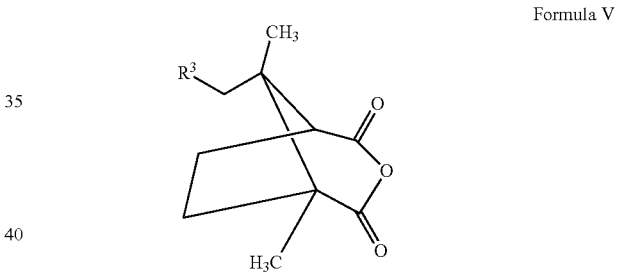

Formula V with a reducing agent, and subjecting the in situ formed reaction mixture to dehydration in the presence of a dehydrating agent.

In a preferred embodiment, the dehydrating and reducing agents may be selected as described hereinabove.

The schematic representation of the process of the invention is shown below in Scheme 1.

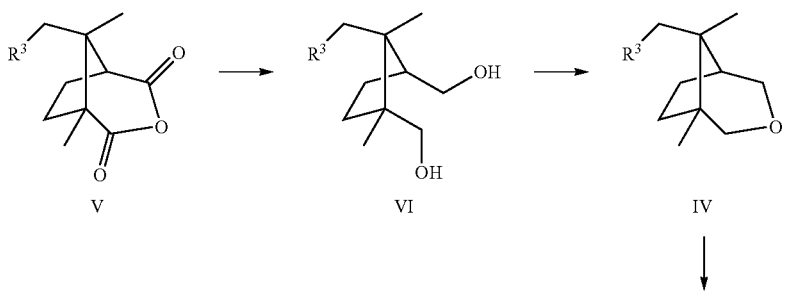

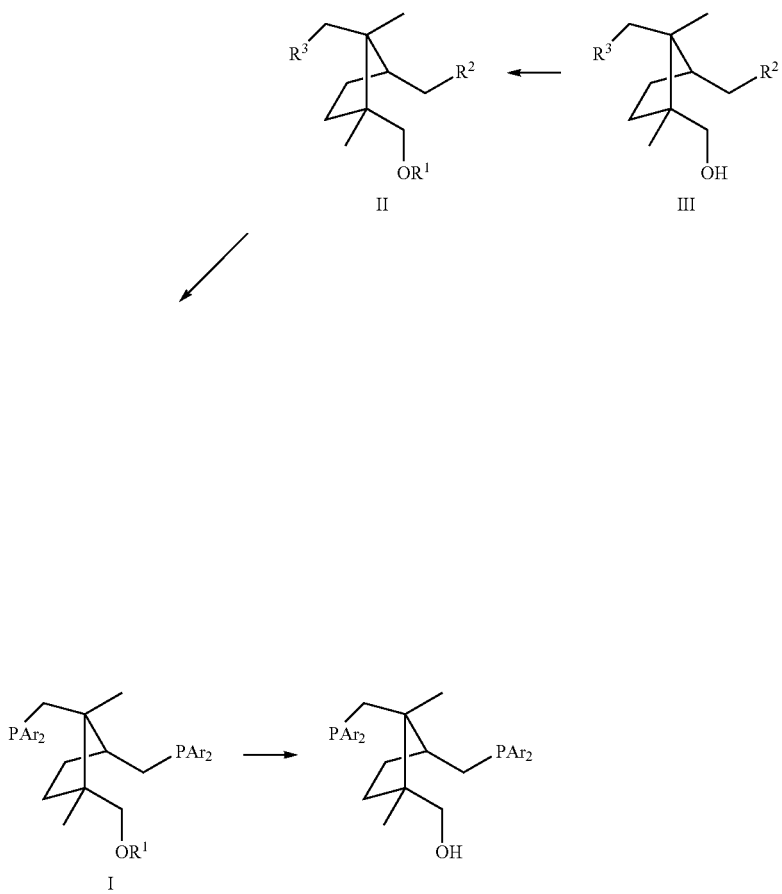

EXAMPLES

Preparation of Formula VI

The cyclic anhydride V ($R^3$=Br, 3.5 gm, 13.3 mmol) was dissolved in dry ether (200 ml) and stirred. The solution was cooled to 20° C. and added Lithium aluminum hydride (2.1 gm, 55.2 mmol) in small portions with continuous stirring. The reaction mixture was then heated to reflux for five hours and then cooled to 25° C. Tetrahydrofuran (THF) (100 ml) was added to the reaction mass followed by careful and slow addition of water (10 ml). The reaction mixture was filtered and the filtrate was concentrated on rotary evaporator to obtain solid mass which was crystallized from chloroform to get the desired product VI in 77.4% yield (2.6 gm, 10.3 mmol, m.p. 116-119° C.).

Example 2

Preparation of Formula IV

Compound VI ($R^3$=Br, 13 gm, 51.79 mmol) was dissolved in carbon tetrachloride (225 ml) and stirred. Triphenyl phosphine (30 gm, 114.5 mmol) was added and stirred. The reaction mixture was further stirred under reflux for 24 hours. It was cooled to 25° C. and n-hexane (200 ml) was added. The precipitated triphenyl phosphine oxide was filtered. The filtrate was concentrated on rotary evaporator to get the solid crude product (12 gm). The product was purified by column chromatography using n-Hexane:Ethyl acetate as eluent (9:1). The desired fraction was evaporated on rotary evaporator to get pure product IV (8 gm, 34.33 mmol, yield 71.8%).

Example 3

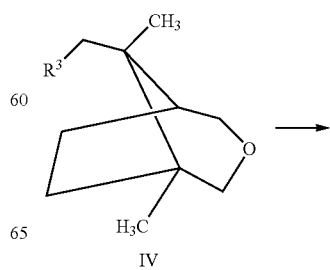

-continued

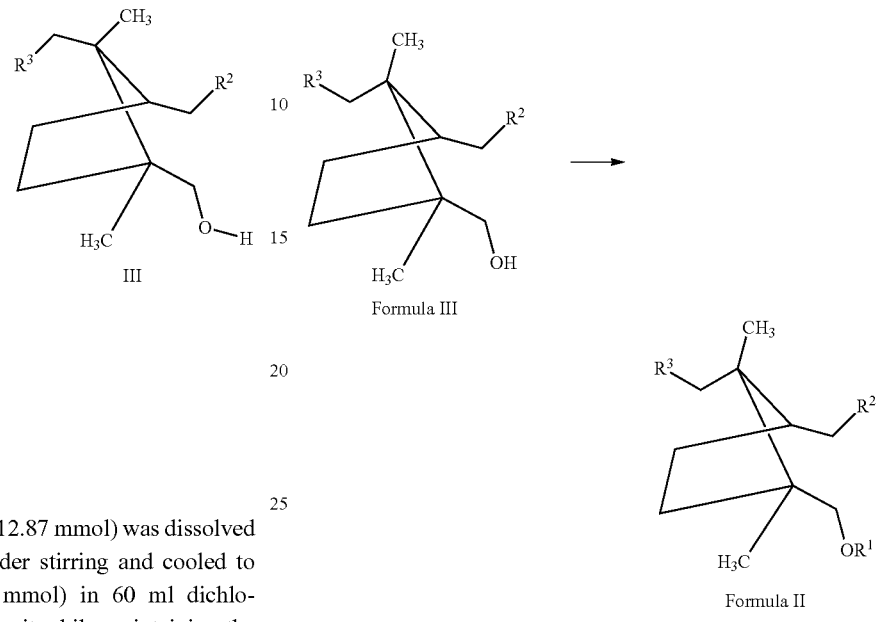

III

The compound of formula IV (12.87 mmol) was dissolved in dichloromethane (100 ml) under stirring and cooled to −10° C. Boron trihalide (23.9 mmol) in 60 ml dichloromethane was gradually added to it while maintaining the temperature. The temperature was then allowed to come to 25° C. and then the reaction mixture was maintained at 60° C. for 1-2 hours. It was then cooled to 0° C. and 10% aqueous sodium hydroxide solution (150 ml) was added and stirred for 1.5 hours. The layers were separated and the organic layer was washed with brine followed by water and dried over sodium sulfate. The organic layer was evaporated on rotary evaporator to get the crude product, which was purified by column chromatography using n-Hexane:Ethyl acetate (95:5) to get compound of formula III.

Table 1 lists the number of compounds of formula III having various substitutions prepared by the process of Example 1.

Example 4

The hydroxyl groups in the compound of formula III may be protected using known processes in the art to arrive at further compounds of the present invention.

Formula III

Formula II

The compound of formula III above (13.37 mmol) was dissolved in dichloromethane (50 ml) and stirred. Suitable protecting reactant (20.06 mmol) was added to it followed by addition of suitable catalyst (0.668 mmol). The reaction mixture was stirred at room temperature for 10-12 hr. The reaction was monitored by TLC. After completion of the reaction, water was added and the layers were separated and the organic layer was washed with water and dried over sodium sulfate. The solvent was evaporated on rotary evaporator to get the product compound of formula II.

Table 2 lists the number of compounds of formula II having various substitutions prepared according to the process discussed above.

| S No. | $R^2$ | $R^3$ | Reagent | MP/BP | IR (Cm$^{-1}$) | NMR (δ, ppm) | Yield/ properties |
|---|---|---|---|---|---|---|---|
| 1 | Cl | Br | Boron trichloride | 63-66° C. | 3369, 2960, 2865, 1450, 1425, 1375, 1245, 1024, , 677 | 0.83 (s, 3H,) 1.1(s3H), 1.8 (s, 2H), 2.9 (s, 1H), 1.4-2.6 (m, 5H) 3.5-3.9 (m, 4H) | 53%/solid |
| 2 | Br | Br | Boron tribromide | 55-58° C. | 3372, 2967, 2881, 1457, 1426, 1376, 1244, 1019, 710, 637 | 0.79 (s, 3H,) 1.1(s, 3H), 2.0 (s, 2H), 2.25(s, 1H,), 1.4-2.5(m, 5H), 3.4-3.8(m, 4H) | 65%/solid |
| 3 | I | Br | Boron tribromide and Sodium Iodide | viscous liquid | 3374, 2958, 2873, 1459, 1428, 1377, 1249, 1189, 1024, 651, 540 | 0.9(s, 3H,) 1.1(s, 3H), 1.7(s, 2H), 2.6(s, H), 1.38-2.45(m, 5H), -, 3.4-3.8(m, 4H) | 72%/ viscous liquid |

| S No. | Protecting reagent | Catalyst | R² | R¹ | R³ | BP | IR (Cm⁻¹) | NMR (δ, ppm) | Yield and properties |
|---|---|---|---|---|---|---|---|---|---|
| 4 | Tetrahydro pyran | Pyridinium p-toluene sulfonate | Br | THP | Br | 135-140° c. | 3054, 2949, 2876, 1422, 1265, 1032, 896, 740, 705 | 0.83 (s, 3H), 1.13 (s, 3H) 1.5-2.6 (m, 11H) 3.4-4.0 (m, 4H) 3.5 (m, 2H) 3.8 (m, 2H) 4.2 (t. 1H) | 95%./ Oil |
| 5 | t-Butyl dimethyl silyl chloride | Imidazole | Br | TB DMS | Br | 252-255° c. | 2955, 2930, 2874, 1467, 1383, 1253, 1088, 937, 839, 776, 640 | 0.1 (s, 6H), 0.8 (s, 9H) 1.0(d, 6H), 1.2-1.7 (m, 5H) 3.3 (d, 1H), 3.5-4.0 (m,4H), 4.1(t, 1H) | 58.5%/ Viscous mass |
| 6 | Benzoyl chloride | Dimetyl amino pyridine | Br | Benzoyl | Br | 260-265° c. | 2962, 2870, 1719, 1450, 1273, 1112, 1069, 1025, 175 | 0.76(s, 3H), 1.2 (s, 3H), 1.4-2.6(m, 5H), 3.4 (s 2H) 3.5-4.0 (m, 4H) 7.4-8.0 (m, 5H) | 44.78/ Oil |
| 7 | Trifluoro acetic anhydride | None | Br | Trifluoro acetyl | Br | 270-274° c. | 2970, 2860, 1784, 1464, 1402, 1382, 1346, 1223, 1158, 774, 733 | 0.85 (s, 3H), 1.12 (s, 3H), 1.4-2.7 (m, 5H), 3.6 (s, 2H), 3.6-4.0 (m, 4H) | 91%/ Viscous Oil |
| 8 | Acetic anhydridel | Dodeca Tungsto-phosphoric acid | Br | Acetyl | Br | 250-255° c. | 2966, 2877, 1739, 1464, 1433, 1379, 1238, 1034, 982, 709, 640 | 0.95 (s, 3H), 1.14 (s, 3H), 2.1 (s, 3H), 1.3-2.7 (m, 5H), 3.3-3.7 (m, 4H). 3.8 (s, 2H) | 79.3%/ Viscous oil |
| 9 | Tetrahydro pyran 1 | Pyridinium p-toluene sulfonate | Cl | THP | Br | 142-148 | 3050, 2950, 2875, 1420, 1261, 1030, 890, 735, 700 | 0.99 (s, 3H), 1.10 (s, 3H), 1.5-2.5 (m, 11H), 3.4-4.0 (m, 4H), 4.1 (t, 1H), 3.6 (m, 2H), 4.0 (m, 2H) | 46.0%/ oil |
| 10 | t-Butyl dimethyl silyl Chloride | Imidazole | Cl | TB DMS | Br | 248-252 | 2955, 2936, 2875, 1467, 1388, 1258, 1090, 935, 835, 775 640 | 0.1 (s, 6H), 0.9 (s, 9H), 1.0 (d, 6H), 1.2-1.6 (m, 5H), 3.4 (d, 1H), 3.5-4.0 (m, 4H), 4.2 (t. 1H) | 48.0%/ oil |
| 11 | Benzoyl chloride | Dimetyl amino pyridine | Cl | Benzoyl | Br | 262-268 | 2960, 2872, 1720, 1452, 1275, 1109, 1067, 1023, 720 | 0.78 (s, 3H), 1.3 (s, 3H), 1.5-2.5 (m, 5H), 3.3 (s, 2H), 3.5-4.0 (m, 4H), 7.5-8.4 (m, 5H) | 45.2%/ oil |
| 12 | Trifluoro acetic anhydride | None | Cl | Trifluoro acetyl | Br | 268-272 | 2965, 2862, 1780, 1465, 1410, 1385, 1345, 1225, 1160, 770, 720 | 0.9 (s, 3H), 1.12 (s, 3H), 1.4-2.5 (m, 5H), 3.5 (s, 2H), 3.6-4.1 (m, 4H) | 89.0%/ Viscous oil |
| 13 | Acetic anhydride | Dodeca Tungstoph osphoric acid | Cl | Acetyl | Br | 250-256 | 2960, 2873, 1735, 1462, 1420, 1365, 1250, 1030, 970, 700, 630 | 0.87 (s, 3H), 1.15 (s, 3H), 2.0 (s, 3H), 1.5-2.5 (m, 5H), 3.3 (s, 2H), 3.4-4.0 (m, 4H) | 75.3%/ oil |
| 14 | Tetrahydro pyran | Pyridinium p-toluene sulfonate | I | THP | Br | 148-152° | 3040, 2941, 2864, 1425, 1265, 1032, 880, 720, 705 | 1.0 (s, 3H), 1.07 (s, 3H), 1.4-2.7 (m, 11H), 3.4-4.3 (m, 4H), 3.5 (m, 2H), 4.0(m, 2H), 4.1(t, 1H) | 49.18%/ oil |
| 15 | t-Butyl dimethyl silyl chloride | Imidazole | I | TB DMS | Br | 240-248 | 2940, 2930, 2857, 1476, 1382, 1253, 1092, 930, 830, 745, 622 | 0.2 (s, 6H), 0.9 (s, 9H), 1.2 (d, 6H), 1.4-1.8 (m, 5H), 3.3 (d, 1H), 3.5-4.2 (m, 4H) 4.3 (t, 1H) | 40.74%/ Viscous oil |
| 16 | Benzoyl chloride | Dimetyl amino pyridine | I | Benzoyl | Br | 258-263° | 2957, 2872, 1720, 1598, 1378, 1313, 1173, 1110, 996, 708, 640, 612 | 0.8 (s, 3H), 1.2 (s, 3H), 1.5-2.4 (m, 5H) 3.3 (s, 2H) 3.6-4.1 (m, 4H), 7.6-8.8(m, 5H) | 39.06%/ oil |
| 17 | Trifluoro acetic nahydride | None | I | Trifluoro acetyl | Br | 268-273° | 2964, 2873, 1784, 1462, 1381, 1348, 1222, 1162, 1085, 774, 732, 651 602 | 1.0 (s, 3H), 1.2 (s, 3H), 1.5-2.5 (m, 5H), 3.3 (s, 2H) 3.4-3.8 (m, 4H) | 66.7%/ oil |
| 18 | Acetic anhydride | Dodeca Tungsto-phosphoric acid | I | Acetyl | Br | 220-228° | 2963, 2874, 1738, 1463, 1426, 1378, 1238, 1080, 1030, 973, 755, 655, 605 | 0.91 (s, 3H), 1.3 (s, 3H), 1.3-1.9 (m, 5H), 2.2 (s, 3H), 3.4 (s, 2H) 3.5-4.0 (m, 4H) | 54.55%/ oil |
| 19 | Tetrahydro pyran | Pyridinium p-toluene sulfonate | OTs | THP | Br | 255-262 | 2942, 2870, 1400, 1245, 1020, 890, 742, 697 | 0.85-1.05 (m, 6H), 1.1-2.4 (m, 11H), 2.44 (s, 3H), 3.0-4.0 (m, 6H), 4.28 (dd, 1H), 4.5 (m, 2H), 7.33 (d, 2H), 7.76 (dd, 2H) | 25.0%/ Viscous oil |

Example 5

The compounds of the present invention were conveniently used to prepare the target hydroxyphosphine ligands. The compounds of the present invention were conveniently reacted with alkali metal salts of diaryl phosphide to obtain intermediate compounds, which were conveniently deprotected to the target hydroxyphosphine ligands.

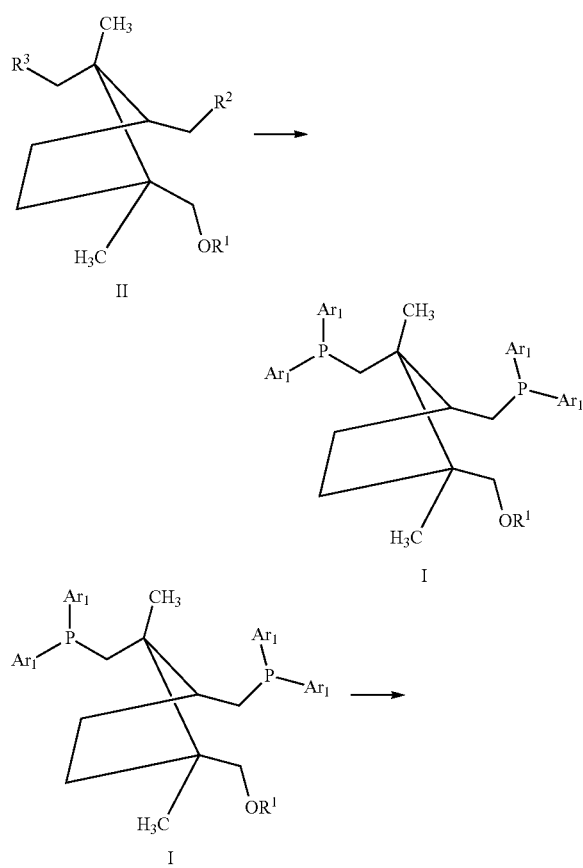

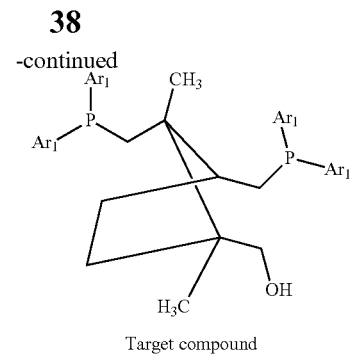

Target compound

The following compounds were prepared using the reaction conditions tabulated as hereunder. The compound of formula II (9.04 mmol) was dissolved in THF (50 mL). The mixture was cooled to −50° C. and lithium diphenyl phosphide solution (30% in THF, 39.47 mmol) was added under nitrogen blanket. The reaction mass was stirred at room temperature for 12-15 hours. The reaction mass was heated to reflux for 2 hours. The mass was further cooled to 0-5° C. and ice water was added to it. The product was extracted in chloroform and organic layer was washed with water and dried over sodium sulfate. The solvent was removed under vacuum and concentrated mass kept at 0-5 torr at 55° C. for 2 hours.

The concentrated mass was dissolved in a solvent (25 ml) and deprotection reagent (1 mmole %) was added. The mixture was stirred at desired temperature for 10-12 hours. The reaction was monitored by TLC after completion of the reaction. The solvent was removed under vacuum. The residue was purified by column chromatography using n-hexane: ethyl acetate 90:10.

The target compound was prepared using the compounds of formula II using the process described above.

TABLE 3

| S No. | $R^1$ | R3 | R2 | Diaryl Phophine reagent | Deprotection Catalyst, Solvent, Temp | Target Compound P(Ar1) | Yield and Properties | NMR |
|---|---|---|---|---|---|---|---|---|
| 36 | THP | Br | I | PPh2Li | PPTS, Ethyl alcohol 50° C. | P(Ph2)2 | 82%, viscous liquid | 0.92 (s, 3H), 1.02 (s, 3H), 1.15-1.50 (m, 3H), |
| 37 | t-Butyl dimethyl silyl | Br | I | PPh2Li | Decaborane, Methanol, Ambient | P(Ph2)2 | 80%, viscous liquid | 1.9-2.0(m, 1H), 2.19-2.32(m, 2H), 2.4(dd, 1H), |
| 38 | Benzoyl | Br | I | PPh2Li | KCN, Methanol, Reflux | P(Ph2)2 | 81%, viscous liquid | 2.65(dd, 1H), 3.3(d, 1H), 3.48(s, 1H) |
| 39 | THP | Br | Br | PPh2Li | PPTS, Ethyl alcohol 50° C. | P(Ph2)2 | 85%, viscous liquid | 3.75 (d, 1H) 6.95-7.1 (m, 12H), 7.57(t, 2H), |
| 40 | t-Butyl dimethyl silyl | Br | Br | PPh2Li | Decaborane, Methanol, Ambient | P(Ph2)2 | 85% viscous liquid | 7.58-7.62(m, 4H), 7.75(t, 2H) |
| 41 | Benzoyl | Br | Br | PPh2Li | KCN, Methanol, Reflux | P(Ph2)2 | 83%, viscous liquid | 0.84 (s, 3H), 0.92-0.96 (m, 12H), 1.01-1.05 (m, 12H), 1.1(s, 3H), |
| 42 | THP | Br | I | P(3,5 Xylyl)2Li | PPTS, Ethyl alcohol 50° C. | P(3,5 Xylyl)$_2$ | 52%, viscous liquid | 1.21-1.56 (m, 3H), 1.98-2.05(m, 1H), 2.21-2.35(m, 2H), |
| 43 | t-Butyl dimethyl silyl | Br | I | P(3,5 Xylyl)2Li | Decaborane, Methanol, Ambient | P(3,5 Xylyl)$_2$ | 50%, viscous liquid | 2.4(dd, 1H), 2.65(dd, 1H), 3.45(d, 1H), |
| 44 | Benzoyl | Br | I | P(3,5 Xylyl)2Li | KCN, Methanol, Reflux | P(3,5 Xylyl)$_2$ | 42%, viscous liquid | 3.48 (s, 1H) 3.77 (d, 1H) 6.98-7.15 (m, 12H), |
| 45 | THP | Br | Br | P(3,5 Xylyl)2Li | PPTS, Ethyl alcohol 50° C. | P(3,5 Xylyl)$_2$ | 55%, viscous liquid | 7.42(t, 2H), 7.58-7.62(m, 4H), 7.85(t, 2H) |

TABLE 3-continued

| S No. | R¹ | R3 | R2 | Diaryl Phophine reagent | Deprotection Catalyst, Solvent, Temp | Target Compound P(Ar1) | Yield and Properties | NMR |
|---|---|---|---|---|---|---|---|---|
| 46 | t-Butyl dimethyl silyl | Br | Br | P(3,5 Xylyl)2Li | Decaborane, Methanol, Ambient | P(3,5 Xylyl)$_2$ | 57% viscous liquid | |
| 47 | Benzoyl | Br | Br | P(3,5 Xylyl)2Li | KCN, Methanol, Reflux | P(3,5 Xylyl)$_2$ | 60%, viscous liquid | |

Although the invention has been shown and described with reference to certain preferred and alternate embodiments, the invention is not limited to these specific embodiments. Minor variations and insubstantial differences in the various combinations of substituents and their relative positioning to each other may occur to those of ordinary skill in the art while remaining within the scope of the invention as claimed and equivalents.

The invention claimed is:

1. A compound of formula II:

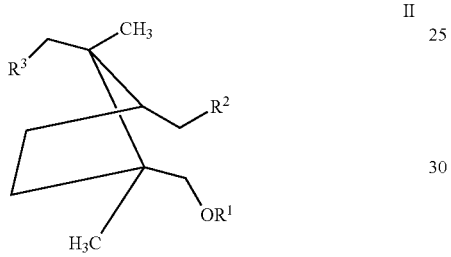

II wherein:

$R^1$ is hydrogen or Z;

$R^2$ and $R^3$ are same or different and are independently selected from F, Cl, Br, I;

Z is a hydroxyl protecting group selected from tetrahydro-2H-pyran-2-yl; tetrahydro-2H-pyran-2-one-3-yl; tetrahydro-2H-pyran-2-methoxy-6-yl; tetrahydro-2H-pyran-2-ethoxy-6-yl; Si(t-Bu)Me$_2$; and —C(O)Ph.

2. The compound as claimed in claim 1, wherein $R^1$ is hydrogen.

3. The compound as claimed in claim 1, wherein $R^1$ is tetrahydro-2H-pyran-2-yl.

4. The compound as claimed in claim 1, wherein $R^1$ is Si(t-Bu)Me$_2$.

5. The compound as claimed in claim 1, wherein $R^1$ is —C(O)Ph.

6. The compound as claimed in claim 1, wherein $R^2$ is Br.

7. The compound as claimed in claim 1, wherein $R^3$ is Br.

8. A process of preparing a compound of formula II:

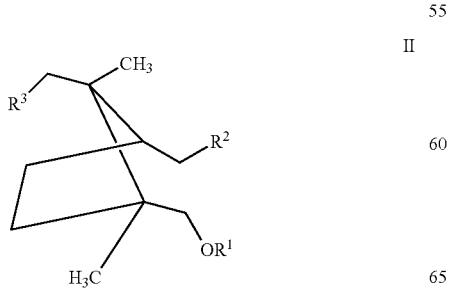

II where:

$R^1$ is hydrogen or Z;

$R^2$ and $R^3$ are same or different and are independently selected from F, Cl, Br, I;

Z is a hydroxyl protecting group selected from tetrahydro-2H-pyran-2-yl; tetrahydro-2H-pyran-2-one-3-yl; tetrahydro-2H-pyran-2-methoxy-6-yl; tetrahydro-2H-pyran-2-ethoxy-6-yl;

Si(t-Bu)Me$_2$; and —C(O)Ph;

wherein said compound of formula II is obtained by protecting the hydroxyl group of the compound of formula III:

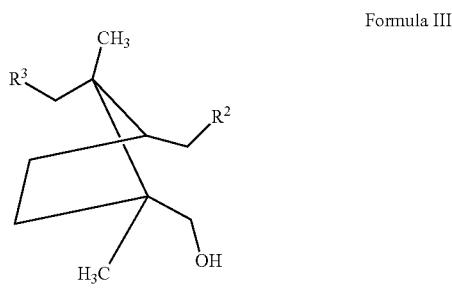

Formula III wherein said compound of formula III is obtained by hydro-halogenating a compound of formula IV:

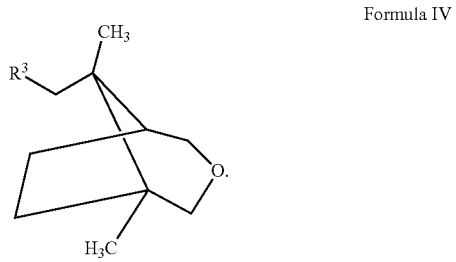

Formula IV

9. The process as claimed in claim 8, wherein said compound of formula IV is obtained by reducing a compound of formula V:

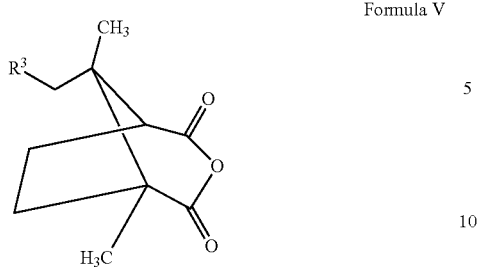
Formula V
with a reducing agent to obtain a compound of formula VI:
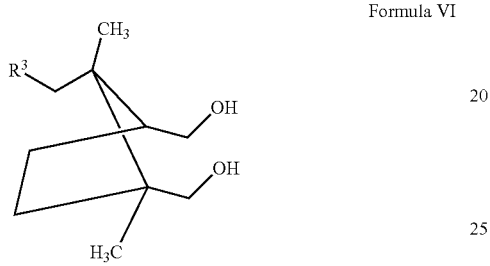
Formula VI
and dehydrating the compound of formula VI in the presence of a dehydrating agent.
* * * * *